(12) United States Patent
Park et al.

(10) Patent No.: US 8,087,151 B2
(45) Date of Patent: Jan. 3, 2012

(54) GAS SENSOR HAVING ZINC OXIDE NANO-STRUCTURES AND METHOD OF FABRICATING THE SAME

(75) Inventors: Rae-Man Park, Daejeon (KR); Sang-Hyeob Kim, Daejeon (KR); Jonghyurk Park, Daejeon (KR); Sunglyul Maeng, Cheongju (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 442 days.

(21) Appl. No.: 12/373,908

(22) PCT Filed: Apr. 3, 2007

(86) PCT No.: PCT/KR2007/001619
§ 371 (c)(1),
(2), (4) Date: Jan. 15, 2009

(87) PCT Pub. No.: WO2008/010638
PCT Pub. Date: Jan. 24, 2008

(65) Prior Publication Data
US 2010/0012919 A1    Jan. 21, 2010

(30) Foreign Application Priority Data
Jul. 18, 2006  (KR) .................... 10-2006-0067095

(51) Int. Cl.
*G01N 27/12*  (2006.01)

(52) U.S. Cl. ............. 29/592.1; 422/83; 422/88; 422/94; 422/98; 73/23.31; 73/23.32; 73/31.05; 73/31.06

(58) Field of Classification Search ............... 73/23.3, 73/23.31, 23.32, 23.34, 31.05, 31.06; 29/592.1, 29/621; 422/83, 88, 94, 98
See application file for complete search history.

(56) References Cited

U.S. PATENT DOCUMENTS

| 5,149,596 | A  | * | 9/1992 | Smith et al. | .................... 428/656 |
| 6,849,911 | B2 | * | 2/2005 | Monty et al. | .................... 257/414 |
| 7,104,111 | B2 | * | 9/2006 | Monty et al. | .................... 73/23.2 |

(Continued)

FOREIGN PATENT DOCUMENTS

JP    2006-102936    4/2006

(Continued)

OTHER PUBLICATIONS

Fan et al., "Semiconductor Nanowires: From Self-Organization to Patterned Growth", Small Journal, vol. 2, No. 6, 2006.*

(Continued)

*Primary Examiner* — David Rogers
(74) *Attorney, Agent, or Firm* — Rabin & Berdo, P.C.

(57) ABSTRACT

A gas sensor includes zinc oxide nano-structures formed on a substrate, a plurality of metal islands coated on a surface of each zinc oxide nano-structure and separated from one another, a first electrode electrically connected to one end of each zinc oxide nano-structure through the substrate, a second electrode electrically connected to the other end of each zinc oxide nano-structure, and a current variation-measuring unit electrically connected to each of the first electrode and the second electrode so as to measure a variation in the amount of current flowing between the first electrode and the second electrode. In order to form the plurality of metal islands on the zinc oxide nano-structures, a solution of metal components of a metal material is coated on the surface of each zinc oxide nano-structure.

14 Claims, 2 Drawing Sheets

U.S. PATENT DOCUMENTS

| | | | |
|---|---|---|---|
| 7,186,381 B2* | 3/2007 | Penner et al. | 422/98 |
| 7,199,029 B2* | 4/2007 | Conley et al. | 438/478 |
| 7,235,475 B2* | 6/2007 | Kamins | 438/618 |
| 7,237,429 B2* | 7/2007 | Monty et al. | 73/23.2 |
| 7,276,389 B2* | 10/2007 | Kim et al. | 438/34 |
| 7,287,412 B2* | 10/2007 | Ng et al. | 73/23.31 |
| 7,354,850 B2* | 4/2008 | Seifert et al. | 438/604 |
| 7,402,531 B1* | 7/2008 | Kuekes et al. | 438/755 |
| 7,521,252 B2* | 4/2009 | Carpenter et al. | 436/144 |
| 7,545,010 B2* | 6/2009 | Ichihara et al. | 257/414 |
| 7,545,051 B2* | 6/2009 | Yang et al. | 257/784 |
| 7,569,941 B2* | 8/2009 | Majumdar et al. | 257/798 |
| 7,608,147 B2* | 10/2009 | Samuelson et al. | 117/89 |
| 7,628,959 B2* | 12/2009 | Penner et al. | 422/98 |
| 2005/0069457 A1 | 3/2005 | Huang et al. | |
| 2006/0071207 A1* | 4/2006 | Conley et al. | 257/43 |
| 2006/0102494 A1 | 5/2006 | Chueh et al. | |
| 2007/0066480 A1* | 3/2007 | Moser et al. | 502/346 |
| 2007/0177139 A1* | 8/2007 | Kamins et al. | 356/301 |
| 2008/0230763 A1* | 9/2008 | Zaidi et al. | 257/9 |
| 2009/0033196 A1* | 2/2009 | Cho et al. | 313/309 |
| 2009/0220561 A1* | 9/2009 | Jin et al. | 424/423 |
| 2010/0108132 A1* | 5/2010 | Tsakalakos et al. | 136/256 |
| 2010/0171095 A1* | 7/2010 | Wang et al. | 257/14 |

FOREIGN PATENT DOCUMENTS

| | | |
|---|---|---|
| KR | 2005-0062778 | 6/2005 |
| KR | 2005-0108646 | 11/2005 |
| KR | 2006-0009734 | 2/2006 |
| WO | WO-2008/010638 | 1/2008 |

OTHER PUBLICATIONS

Love et al., "Formation and Structure of Self-Assembled Monolayers of Alkanethiolates on Palladium", Journal of the American Chemical Society, No. 125 (2003), pp. 2597-2609.*

Wang, Hung-Ta et al., "Hydrogen-Selective Sensing at Room Temperature with ZnO Nanorods", Applied Physics Letters 86, 243503 (2005).

* cited by examiner

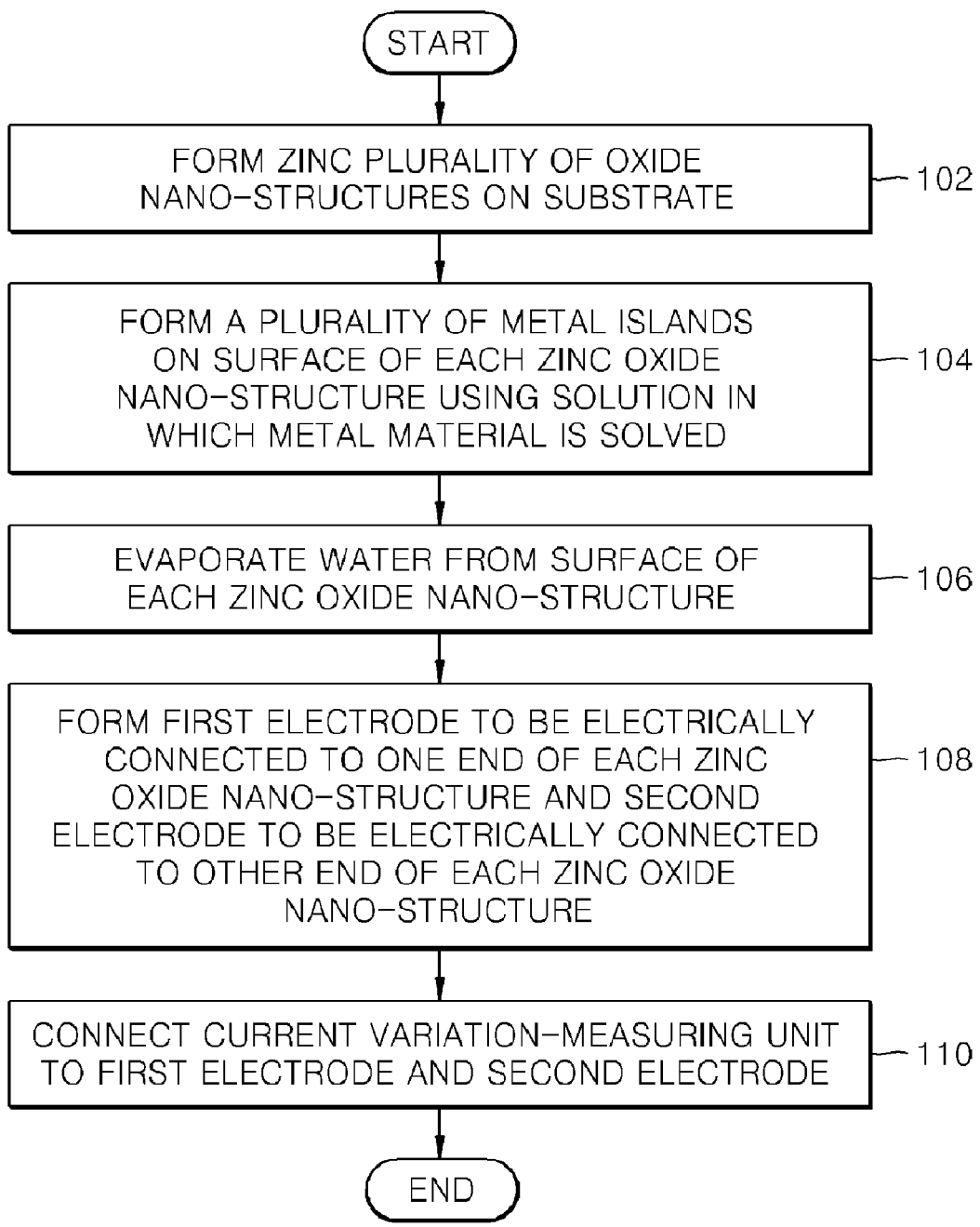

GAS SENSOR HAVING ZINC OXIDE NANO-STRUCTURES AND METHOD OF FABRICATING THE SAME

TECHNICAL FIELD

The present invention relates to a gas sensor having zinc oxide nano-structures and a method of fabricating the same, and more particularly, to a high-sensitivity gas sensor capable of detecting a variety of gases using zinc oxide nano-structures and metal islands coated on the zinc oxide nano-structures and a method of fabricating the same.

BACKGROUND ART

Recently, an environmental problem known as global warming which is caused by the excessive use of fossil fuels has become a serious problem. In addition, people's awareness to the problem of the exhaustion of fossil fuels has increased. To overcome these problems, the development of hydrogen energy which is one kind of alternative energy and the development of a sensor of contamination gas caused by environmental pollution have rapidly progressed. Currently, many technologies for using hydrogen energy have been proposed. However, hydrogen energy is highly explosive, unlike existing energies. Thus, a safety device should be employed when the hydrogen energy is used. To widely use hydrogen energy, a hydrogen detecting technology is required.

DISCLOSURE OF INVENTION

Technical Problem

To date, a variety of research about a contamination gas sensor using nano-wires has been performed. However, it is difficult to widely employ a contamination gas sensor using existing technology.

As an example of conventional technologies for detecting a contamination gas, a technology using a metallic film such as palladium or platinum or a metallic nano-structure has been developed. However, there are many problems in this technology to be overcome such as a reaction time, a reaction concentration or a gas-detecting temperature. Endeavors have been made to use oxide semiconductor nano-wires formed using materials such as zinc oxide or nano-tubes in a gas sensor to solve the problems. In the prior art, sputtering which is a physical deposition method is used when a gas sensor is fabricated. There are also complicated fabricating processes in which expensive equipment is needed or thermal processing is performed at comparatively high temperature, and costs are comparatively high such that it is difficult to widely implement contamination gas sensors.

Technical Solution

The present invention provides a gas sensor in which a variety of gases can be detected with higher sensitivity and which can be widely used.

The present invention also provides a method of fabricating a gas sensor by which a high-sensitivity gas sensor can be fabricated at low cost using a simpler fabricating process.

According to an aspect of the present invention, there is provided a gas sensor, the gas sensor including : a plurality of zinc oxide nano-structures formed on a substrate; a plurality of metal islands coated on a surface of each zinc oxide nano-structure and separated from one another; a first electrode electrically connected to one end of each zinc oxide nano-structure through the substrate; a second electrode electrically connected to the other end of each zinc oxide nano-structure; and a current variation-measuring unit electrically connected to each of the first electrode and the second electrode so as to measure a variation in the amount of current flowing between the first electrode and the second electrode.

Each zinc oxide nano-structure may have a structure of a nano-wire or nano-rod. The metal islands may be formed of one material selected from the group consisting of platinum (Pt), palladium (Pd), nickel (Ni), and cobalt (Co).

According to another aspect of the present invention, there is provided a method of fabricating a gas sensor. In the method, a plurality of metal islands separated from one another on a surface of each of a plurality of zinc oxide nano-structures are formed by coating metal components of a metal material on the surface of each zinc oxide nano-structure in a solution in which the metal material is dissolved. And, a first electrode to be electrically connected to ends of the zinc oxide nano-structures and a second electrode to be electrically connected to the other ends of the zinc oxide nano-structures are formed.

The method may further include, before forming the first electrode and the second electrode, evaporating water from the surface of the zinc oxide nano-structures in which the metal islands are formed.

The solution may include the metal material dissolved in aqua regia. The solution may further include at least one selected from distilled water and basic solution.

The metal material may be a metal powder or a metal organic compound.

The method may further include, before forming the plurality of metal islands, forming the zinc oxide nano-structures on a substrate, wherein the forming of the plurality of metal islands includes dipping the substrate on which the zinc oxide nano-structures are formed in the solution.

ADVANTAGEOUS EFFECTS

In the gas sensor according to the present invention, a plurality of metal islands are formed on a zinc oxide nano-structure and are independently separated from one another on the zinc oxide nano-structure and sensitivity to a gas is improved by the metal islands such that a variety of kinds of gases can be detected. In the method of fabricating a gas sensor according to the present invention, a wet method is used to form the metal islands on the surface of the zinc oxide nano-structure. Thus, a high-sensitivity gas sensor can be fabricated with low costs using a simpler fabrication process.

DESCRIPTION OF DRAWINGS

The above and other features and advantages of the present invention will become more apparent by describing in detail exemplary embodiments thereof with reference to the attached drawings in which:

FIG. 3 is a flowchart illustrating a method of fabricating a gas sensor according to an embodiment of the present invention.

BEST MODE

The present invention will be described more fully hereinafter with reference to the accompanying drawings in which exemplary embodiments of the invention are shown.

Figure 1:
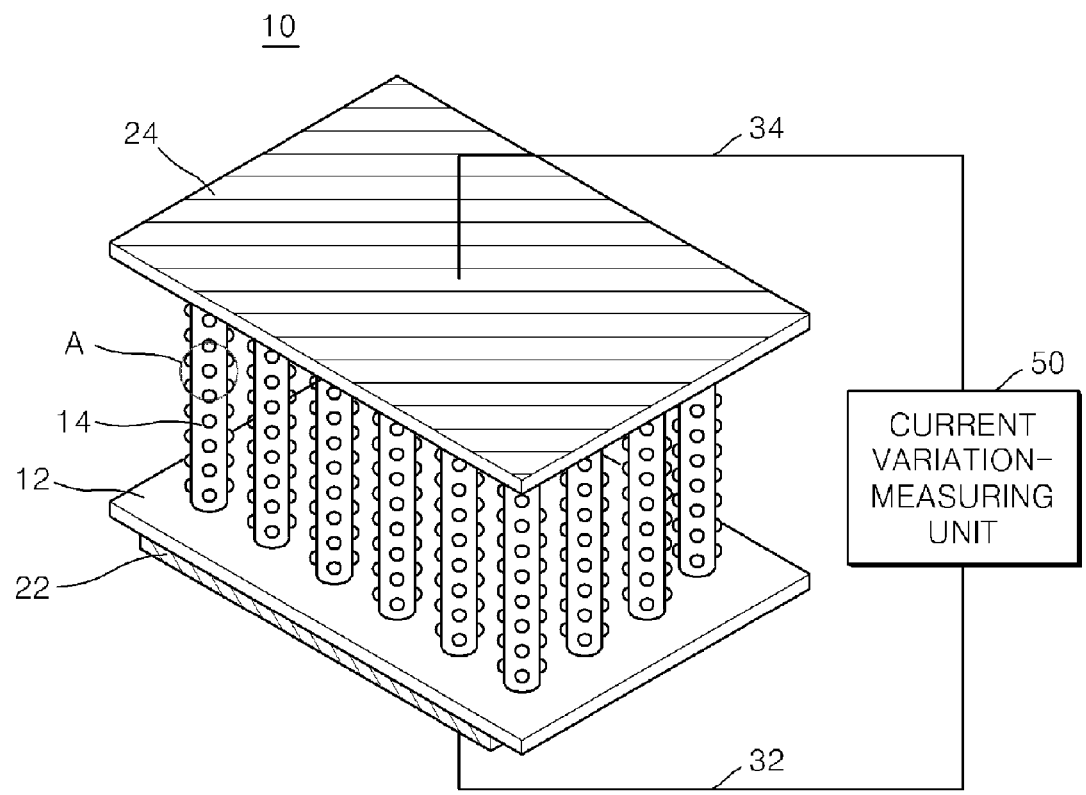
FIG. 1 is a schematic perspective view of a gas sensor according to an embodiment of the present invention.

FIG. 1 is a schematic perspective view of a gas sensor 10 according to an embodiment of the present invention. The gas sensor 10 of FIG. 1 includes a plurality of zinc oxide nano-structures 14 formed on a main surface of a substrate 12. The substrate 12 may be a silicon substrate. Each zinc oxide nano-structure 14 may have a structure of a nano-wire or nano-rod. Each zinc oxide nano-structure 14 may have a diameter of about several tens to several hundreds of nm, for example, from about 10 to 900 nm. In addition, each zinc oxide nano-structure 14 may have a length of several hundreds of nm to several tens of □, for example, from about 500 nm to 50□.

Figure 2:
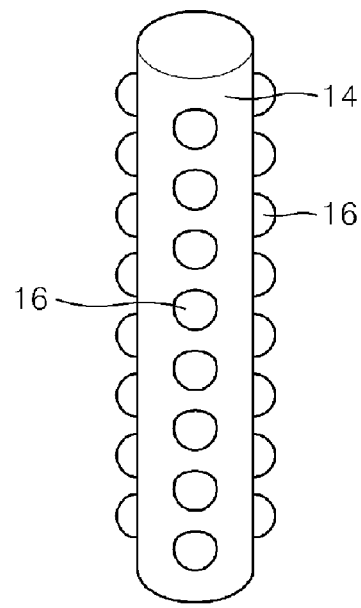
FIG. 2 is a perspective view of a single zinc oxide nano-structure of the gas sensor of FIG. 1.

FIG. 2 is a perspective view of a single zinc oxide nano-structure 14 of the gas sensor 10 of FIG. 1. Referring to FIGS. 1 and 2, a plurality of metal islands 16 are coated on the surface of the zinc oxide nano-structure 14. The plurality of metal islands 16 are separated from one another on the surface of the zinc oxide nano-structure 14. The metal islands 16 may have a grain size of several to several tens of nm, for example, from about 2 to 50 nm.

The metal islands 16 may be formed of a variety of kinds of metal. For example, the metal islands 16 may be formed of one material selected from the group consisting of platinum (Pt), palladium (Pd), nickel (Ni), and cobalt (Co).

A first electrode 22 is formed on a surface of the substrate 12 opposite to the surface of the substrate 12 on which the plurality of zinc oxide nano-structures 14 are formed. The first electrode 22 is electrically connected to one end of the zinc oxide nano-structures 14 in a state where the substrate 12 is placed between the first electrode 22 and the zinc oxide nano-structures 14. In addition, a second electrode 24 is electrically connected to the other ends of the zinc oxide nano-structures 14. The first electrode 22 and the second electrode 24 are electrically connected to a current variation-measuring unit 50 via electrical wires 32 and 34 connected to the first electrode 22 and the second electrode 24, respectively.

In the gas sensor 10 of FIG. 1, when a gas to be detected is present, the gas is easily absorbed into the metal islands 16 and is ionized, and the ionized gas reacts with the surface of the zinc oxide nano-structure 14. As a result, electric conductivity of the zinc oxide nano-structure 14 varies according to the concentration of the gas to be detected that is present and thus the amount of current flowing between the first electrode 22 and the second electrode 24 changes. The current variation-measuring unit 50 detects a variation in an electric signal according to the variation in the amount of current so that the presence of a gas and the concentration of the gas can be detected from the detected variation in the electric signal.

The gas sensor 10 according to the present invention shows a high sensitivity in detecting a minor variation in the concentration of a gas to be detected. In particular, when the gas to be detected is hydrogen ($H_2$), even of a very low concentration less than or equal to about 10 ppm, the gas can be detected with high accuracy. In addition, the gas sensor 10 of FIG. 1 can detect a variety of kinds of gases such as $H_2$, nitrogen monoxide (NO), nitrogen dioxide ($NO_2$), methane ($CH_4$), carbon dioxide ($CO_2$), hydrogen sulfide ($H_2S$) or ethanol.

Mode for Invention

FIG. 3 is a flowchart illustrating a method of fabricating a gas sensor according to an embodiment of the present invention. Specifically, the method of fabricating a gas sensor will now be described with reference to FIGS. 1, 2, and 3.

In operation 102, a plurality of zinc oxide nano-structures 14 are formed on a substrate 12, for example, on a silicon substrate, using a general method. As described with reference to FIG. 1, each zinc oxide nano-structure 14 may have a structure including a nano-wire or nano-rod.

In operation 104, a plurality of metal islands 16 are formed on the surface of each zinc oxide nano-structure 14 using a solution in which a metal material is dissolved. The plurality of metal islands 16 are obtained by coating the solution in which the metal material is dissolved on each zinc oxide nano-structure 14. The metal islands 16 are separated from one another on the surface of each zinc oxide nano-structure 14.

More specifically, the solution in which the metal material is dissolved may be prepared as below. First, the metal material to be coated on each zinc oxide nano-structure 14 is dissolved in aqua regia. In this case, the aqua regia may be kept at a temperature in the range of about 50-100° C. The metal material may be a metal powder. Alternatively, the metal material may be one metal organic compound selected from the group consisting of $H_2PtCl_6$, $MeCpPtMe_3$, $Pt(acac)_2$, $Pd_2(allyl)_2Cl_2$, and $Pd(C_3H_5)(C_5H_5)$ where Me=methyl, Cp=cyclopentadienyl, acac=acetyl-acetone.

The concentration of metal in the solution may be controlled to be from about 1-70 wt % based on a total weight of the solution. The aqua regia in which the metal is dissolved can be diluted so as to control the concentration of the metal in the solution to a desired value. In this case, in order to dilute the solution, distilled water or a basic solution, for example, ammonia water, may be added to the aqua regia in which the metal is dissolved.

In order to form the plurality of metal islands 16, a substrate 12 on which the zinc oxide nano-structures 14 are formed is dipped in the solution in which the metal having a desired concentration is dissolved. While the metal islands 16 are formed on the zinc oxide nano-structures 14, the solution is kept in the temperature range of about 30-100□. The zinc oxide nano-structures 14 may be dipped in the solution for a predetermined time, for example, for about one second to one minute, so as to form the metal islands 16 on the zinc oxide nano-structures 14. The size of the metal islands 16 formed may depend on the amount of time the zinc oxide nano-structures 14 are dipped or the concentration of the metal in the solution. Thus, a dipping time and the concentration of the metal in the solution need to be properly controlled so as to obtain the metal islands 16 having a proper size.

In operation 106, water is evaporated from the surface of the zinc oxide nano-structures 14 in which the metal islands 16 are formed. To this end, the zinc oxide nano-structures 14 are kept from room temperature to 100° C., preferably, from about 30-60° C. for about 1-30 minutes until water is completely evaporated from the surface of the zinc oxide nano-structures 14 after the zinc oxide nano-structures 14 in which the metal islands 16 are formed are taken out from the solution.

In operation 108, a first electrode 22 is formed to be electrically connected to ends of the zinc oxide nano-structures 14 and a second electrode 24 is formed to be electrically connected to the other ends of the zinc oxide nano-structures 14.

In operation 110, a current variation-measuring unit 50 is electrically connected to the first electrode 22 and the second electrode 24.

INDUSTRIAL APPLICABILITY

As described above, in the gas sensor according to the present invention, a plurality of metal islands are formed on a plurality of zinc oxide nano-structures and the islands are formed separated from one another on the zinc oxide nano-structures. In the gas sensor according to the present invention, sensitivity to a gas is improved by the metal islands such that a gas to be detected can be detected with high sensitivity. In addition, a variety of kinds of gases can be detected. Gases can be detected at comparatively high detecting temperatures.

In addition, in the method of fabricating a gas sensor according to the present invention, a wet method is used to form the metal islands on the surface of the zinc oxide nano-structures. Thus, expensive equipment or subsequent thermal processing which has been required in a conventional method can be omitted, and the metal islands can be formed on the surface of the zinc oxide nano-structures simply, at low cost, and effectively. Thus, a high-sensitivity gas sensor can be fabricated at low cost using a simpler fabrication process.

While the present invention has been particularly shown and described with reference to exemplary embodiments thereof, it will be understood by those skilled in the art that various changes in form and details may be made therein without departing from the spirit and scope of the invention as defined by the following claims.

Sequence List Text

The invention claimed is:

1. A method of fabricating a gas sensor, the method comprising:
    forming a plurality of metal islands separated from one another on a surface of each of a plurality of zinc oxide nano-structures by coating a solution in which a metal material is dissolved on the surface of each zinc oxide nano-structure; and
    forming a first electrode to be electrically connected to ends of the zinc oxide nano-structures and a second electrode to be electrically connected to the other ends of the zinc oxide nano-structures.

2. The method of claim 1, further comprising, before forming the first electrode and the second electrode, evaporating water from the surfaces of the zinc oxide nano-structures in which the metal islands are formed.

3. The method of claim 1, wherein the metal material is a metal powder.

4. The method of claim 1, wherein the solution is kept in a temperature range of 30-100° C. while the plurality of metal islands are formed.

5. The method of claim 1, wherein a concentration of metal in the solution is 1-70 wt % based on a total weight of the solution.

6. The method of claim 1, wherein the zinc oxide nano-structures are dipped in the solution for a period of time in the range of one second to one minute so as to form the plurality of metal islands.

7. The method of claim 1, further comprising, before forming the plurality of metal islands, forming the zinc oxide nano-structures on the substrate, wherein the forming of the plurality of metal islands comprises dipping the substrate on which the zinc oxide nano-structures are formed in the solution.

8. The method of claim 1, wherein the solution comprises the metal material dissolved in aqua regia.

9. The method of claim 8, wherein the solution further comprises at least one selected from distilled water and a base solution.

10. the method of claim 9, wherein the base solution comprises ammonium hydroxide.

11. The method of claim 1, wherein the metal material is a metal organic compound.

12. The method of claim 11, wherein the metal material is formed of one metal organic compound selected from the group consisting of $H_2PtCl_6$, $MeCpPtMe_3$, $Pt(acac)_2$, $Pd_2(allyl)_2Cl_2$, and $Pd(C_3H_5)(C_5H_5)$, where Me=methyl, Cp=cyclopentadienyl, and acac=acetyl-acetone.

13. A gas sensor fabricated by the method of claim 1.

14. The gas sensor of claim 13, wherein the metal islands have a grain size ranging from about 2 nm to about 50 nm.

* * * * *